United States Patent [19]

Ilizarov

[11] Patent Number: 4,978,348
[45] Date of Patent: Dec. 18, 1990

[54] COMPRESSION-DISTRACTION APPARATUS FOR OSTEOSYNTHESIS

[76] Inventor: Gavriil A. Ilizarov, ulitsa Klimova, 41, kv. 38., Kurgan, U.S.S.R.

[21] Appl. No.: 460,906

[22] PCT Filed: May 26, 1988

[86] PCT No.: PCT/SU88/00131
§ 371 Date: Feb. 8, 1990
§ 102(e) Date: Feb. 8, 1990

[87] PCT Pub. No.: WO89/11254
PCT Pub. Date: Nov. 30, 1989

[51] Int. Cl.⁵ ............................................. A61F 5/04
[52] U.S. Cl. ...................................... 606/57; 606/59; 606/105
[58] Field of Search ............................. 606/53, 59, 105

[56] References Cited

U.S. PATENT DOCUMENTS

| | | | |
|---|---|---|---|
| 2,251,209 | 7/1941 | Stader | 606/54 |
| 2,346,346 | 4/1944 | Anderson | 606/56 |
| 2,372,866 | 4/1945 | Tofflemire | 606/54 |
| 2,391,537 | 12/1945 | Anderson | 606/54 |
| 2,393,694 | 6/1946 | Kirschner | 606/57 |
| 2,497,626 | 2/1950 | Persall | 606/54 |
| 3,877,424 | 4/1975 | Murray | 606/54 |
| 3,961,854 | 6/1976 | Jaquet | 606/54 |
| 4,135,505 | 1/1979 | Day | 606/54 |
| 4,360,012 | 11/1982 | McHarrie | 606/54 |
| 4,361,144 | 11/1982 | Slätis | 606/54 |
| 4,620,533 | 11/1986 | Mears | 606/54 |

FOREIGN PATENT DOCUMENTS

| | | |
|---|---|---|
| 3527342 | 9/1987 | Fed. Rep. of Germany . |
| 2559380 | 3/1985 | France . |
| 1161100 | 1/1985 | U.S.S.R. . |
| 2146533 | 4/1985 | United Kingdom . |
| 2168255 | 10/1986 | United Kingdom . |

OTHER PUBLICATIONS

Klinik fur Orthopadische Chirurgie der Universitat Bern, Schweiz, Roland P. Jakob, "Der Kleine Fixateur Externe".

*Primary Examiner*—Robert A. Hafer
*Assistant Examiner*—Michael Brown
*Attorney, Agent, or Firm*—Lilling and Lilling

[57] ABSTRACT

In a compression-distraction apparatus for osteosynthesis, including at least two supporting units (1), each incorporating at least two fixing pins (3) fitted in pin holders (2) which are made as a bolt (4) carrying plates (8) having open slots (10) for the pins (3) to fit and a set of spacer shims (9) and are fitted on a threaded rod (6) with a possibility of moving lengthwise its axis, according to the invention, the bolt (4) of the pin holder (2) has an axial hole (5) through which the main threaded rod (6) is free to pass, and the plates (8) and the spacer shims (9) are shaped as washers set on the bolt (4), the open slots (10) for the pins (3) to fit are made on the end surfaces of the plates (8) and pass along the chord of their circumference on the far side of hole (12) in the washer, and the pins (3) are curved and locked in place in the pin holder (2) in a criss-cross manner.

17 Claims, 6 Drawing Sheets

COMPRESSION-DISTRACTION APPARATUS FOR OSTEOSYNTHESIS

FIELD OF THE INVENTION

The invention relates generally to medical engineering applied in orthopedics and traumatology and more specifically to compression-distraction apparatus for osteosnnthesis.

PRIOR ART

Known in the present state of the art is an externally applied device for orthopedic axial fixation (FR, A, No. 2,559,380), comprising a metallic rod shaped as a parallelepiped carrying two pin clamps. The jaws of the pin clamp are held by a screw, and one of the jaws is longitudinally traversable by virtue of a threaded spindle.

The aforediscussed device enables one to fix tubular bones and carry out longitudinal motion of bone fragments. However, parallel-arranged cantilevered pins are liable to slip off the bone under the effect of a load applied thereto. Besides, the slots made in the clamps and adapted to receive the pins are spaced somewhat apart from one another which is far from being always admissible for a given bone segment.

One prior-art orthopedic apparatus is made use of for treatment of bone lesions, intended for external axial fixation of the injured bone or framents of bone fractures within a wide range of adjustment (GB,A, No. 2,168,255).

The apparatus features a central body made up of three or more components which are movable with respect to one another due to telescopic sliding over each other without a possibility of relative rotation. The body components are provided with an interlocking means which can be actuated independently for each pair of the components.

Moreover, there is provided a power cylinder having at least three elements adapted to be screwed into one another and to move lengthwise a common axis when one of the elements is set in rotation. The elements are situated at the cylinder end and have pins engageable with the eccentric spaces of the cylindrical body.

The apparatus described above is capable of controlline the arrangement of the elements provided with pins, both with respect to one another and to the central body. However, the pins are mounted in the holes of the elements at a definite distance from one another and are therefore inconvenient for use due to impossibility of free selection of the place of installation of the rods in the bone involved. Besides, no provision is made in the orthopedic apparatus for external axial fixation for a possibility of adjusting the angle at which the pins are arranged in the element; furthermore the pins are guided in the dorsipalmar direction which is causative of inujury to the wrist flexor muscles.

For treatment of injuries to the wrist joints use is made of a dynamometric external retainer (GB,A, No. 2,146,533) having two oblong supports, each carrying fixing pins. Both of the supports are interconnected through a universal joint which comprises a number of elements for adjusting the degree of displacement of the distal support with respect to the proximal support. The latter support has a number of holes for receiving the fixing pins and the respective threaded locking elements. The distal support has a plunger to adjust the length of the support. A setting screw adapted to reciprocate in the slot of the distal suppoty is for adjusting the degree of the plunger extension. The dynamometric external retainer discussed above makes it possible to fix the joint of two adjacent bones lengthwise the lateral carpal surface.

Provision is made in the aforesaid retainer for a possibility of adjusting the degree of displacement of the sital support with respect to the proximal one and measuring the displacement length. Apart from that, the pins of the distal support are movable with respect to those of the proximal support. However, the holes for the pins in the retainer supports are spaced a definite specified distance from one another. No provision is made for setting and locking the pins at different angles to the longitudinal axis of the retainer supports. The pins are arranged in the same plane parallel to the longitudinal bone axis. In additional there are greatly impeded the application of the dynamometric external reatiner to the adjacent finger phalanges and its simultaneous placing on the adjacent carpal bones and phalanges.

Prior to setting the fixing pins having threaded ends, a channel is made in the bone involved and then the pin threaded end is fitted therein, which inflicts traumatic lesion upon both soft and bone tissues. Bone resoprtion is liable to occur in the course of treatment which would result in the threaded-end fixing pins slipping off the bone.

When treating bone lesions use is made of external miniretainers (cf. Klinik für orthopädische Chirurgie der Universität Bern, Schweiz, Roland P. Jakob, "Der kleine Fixateur externe").

The retainer comprises rods connected to one another, and threaded-end pins held in pin clamps, the angle of pin setting ranging between 40 and 60 degrees.

The aforesaid device makes it possible to effect controllable reposition and then to fix the injured bones. The pins are held in a plane parallel to the longitudinal axis of the rod carrying the pin clamps, each carrying one pin, which results in increased overall dimensions of the retainer as for length. Besides, bone resorption is liable to occur in the course of treatment, which causes the pin to loose during treatment.

A more perfect device for elongation of short tubular bones (SU,A, No. 1,161,100) is known to provide for a possibility of distraction. The device incorporates a threaded rod carrying pin clamps movably mounted thereon. Each of the pin clamps is made up of a support plate and a pressure plate, and also bolts and washers interposed between the plates. The support plate is mounted on the threaded rod, while the bolts are accommodated in plain holes of the washers and the support plate and in tapped holes of the pressure plate.

However, the device under consideration fails to provide a possibility of varying the guide angle of pins, since the slots in the support and pressure plates cannot assume various angular positions with respect to a plane passing through the longitudinal axes of the threaded rods which in turn does not allow the position of the pins to be corrected in the course of treatment when the bone resorption occurs at the places of bone-to-pins contact, as well as reposition to be carried out, thus making the device applicable for uniting bone fractures. Clinical trials of the device in question have confirmed its limited applicability for osteosynthesis of closely arranged short tubular bones due to relatively large overall dimensions of the device.

DISCLOSURE OF THE INVENTION

The object of the present invention is to provide a compression-distraction apparatus whose construction would make it possible to locate the fixing pins at optimum places of the bone involved, as well to correct the position of the fixing pins in the course of osteosynthesis and the following treatment and to extend its functional capabilities due to reduced overall dimensions and weight.

The aforesaid object is accomplished due to the fact that in a compression-distraction apparatus for osteosynthesis, comprising at least two support units each incorporating at least two fixing pins, one of whose arms crossing over in the bone, while the other arms are secured in pin holders made as a bolt carrying a set of plates having open slots to accept the fixing pins and a stack of spacer shims, the pin holders being fitted on a threaded rod traversably lengthwise the axis thereof and fixable with the aid of nuts, according to the invention, the bolt of the pin holder has an axial hole through which the main threaded rod is free to pass, the plates and spacer shims are shaped as washers mounted on the bolt rotatably about its axis and fixable by a clamping nut, the open slots adapted to receive the fixing pins are provided on the end surfaces of the plates and pass along the chord of their circumference on the far side of the hole in the washer, while the nuts fitted in the main threaded rod are situated on both sides of the bolt ends, and the fixing pins are curved and locked in the pin holder in a criss-cross fashion.

It is expedient that the pin holder of the support unit be provided with a stop screw fitted in a tapped hole made in the head of the pin holder bolt square with the axis of the bolt hole, and that a flat be provided on the main threaded rod lengthwise the latter, said flat being adapted to interact with the stop screw end face.

Provision of the stop screw fitted in the tapped hole of the head of the pin holder bolt of the support unit and intersection of said stop screw with the flat on the main threaded rod lengthwise the latter ensure against rotation of the support unit in the course of its graduated motion lengthwise the axis of the main threaded rod.

It is practicable that a slot be provided on the end face of the head of the pin holder bolt on the side facing the bolt thread, said slot being adapted for accepting the fixing pin.

Provision of such a slot provides for the optimum conditions for fitting the fixing pin and enables one to set and secure the pin in the support unit using the minimized amount of plates and spacer shims.

It is expedient that each of the pin holder plates having an open slot be shaped as a washer having a flat the plane of which is arranged at an angle to the plate and surface and parallel to the slot longitudinal axis, both the flat and the slot lying on the same side of the plate centre hole.

Such a construction arrangement of the pin holder plates of the support unit provides for visual control over the direction of the open slot when setting the fixing pins therein.

It is desirable that through holes be provided in the end surfaces of the pin holder plates and that magnets be accommodated in said holes.

In an embodiment of the invention it is practicable to provide through holes in the end surfaces of the spacer shims of the pin holder and to place magnets therein.

Such embodiments of the invention provide for preliminary short-time retention of the fixing pins in a definite position till they are secured in place completely.

It is expedient that recesses be made on the cylindrical surface of the pin holder plates.

Provision of the recesses simplifies orientation of the open slot in the pin holder plates.

It is possible to bend the arms of the fixing pins at an obtuse angle.

Such a shape of the fixing pins enables one to add to rigidity of the pin holder construction and facilitate criss-cross setting of the fixing pins.

In an embodiment of the invention the arms of the fixing pins may also be curved at an acute angle.

This makes it possible to fit the pin holders onto the pins on the outer side thereof, which is especially convenient with a minimized over all dimensions of the apparatus, and to locate the threaded rod as close to the bone as possible, which adds to the rigidity of the fixing pins and to the magnitude of forces relayed by them.

It is desirable that stops be provided on the pin arms introduced into the bone, aimed at restricting the depth of penetration of a pin into the bone.

Such stops are necessary for preventing the tendons on the wrist palmar surface from injury by limiting the length of the fixing pin introduced into the bone; besides, the stops add to the fixation rigidity, In addition, the apparatus comprising two support units may have an additional support unit mounted on an extra threaded rod movably with respect to the main threaded rod.

Provision of an additional support unit makes it possible to carry out simultaneous treatment of adjacent or side-by-side arranged bones.

In an embodiment of the invention the additional support unit is free to perform relative motion on the additional threaded rod whose longitudinal axis is substantially parallel to that of the main threaded rod, said additional threaded rod being relatively movable lengthwise its own axis.

Such a construction arrangement of the apparatus makes it possible to elongate a short tubular bone articulated to the fragment of the phalangeal stump and located proximally of the latter.

According to another embodiment of the invention the apparatus comprises a plate provided with holes which accept the main and additional threaded rods connected to the aforesaid plate through nuts located on both sides of the plate.

Such a construction arrangement of the apparatus enables one to effect distraction for stretching out a proximally arranged short tubular bone with the aid of either the main or the additional threaded rod.

In another embodiment of the invention the additional support unit is mounted on the additional threaded rod connected to the main threaded rod with a possibility of angular motion.

Such a construction arrangement of the apparatus makes it possible to spread apart closely situated bones simultaneously with stretching-out of the short tubular bone in order to, e.g., widen the interdigital spaces.

According to a further embodiment of the invention the additional threaded rod is articulately connected to one end of a second additional rod whose other end is longitudinally movable and is fixable, by means of nuts, in a bracket provided on the main threaded rod between two support units.

Such a construction arrangement of the apparatus makes it possible to widen the interdigital spaces and at the same time to stretch out one of the short tubular bones, the longitudinal axes of the main and additional threaded rods aligning with the direction of the digitial radii.

According to one more embodiment of the invention, the apparatus has a unit for retraction of soft tissue, comprising a pin curved into a loop whose arms are secured in the pin holder and are free to pass therethrough in a criss-cross fashion so that at least one of the arms of the loop-shaped pin is held to one end of the first additional threaded rod, the other end of which is longitudinally movable in the first perforated plate, wherein one end of the second additional rod is mounted with a possibility of longitudinal motion, while the other end of said rod is longitudinally traversable in the second perforated plate fitted on the main threaded rod with a possibility of relative motion lengthwise its longitudinal axis, both the main threaded rod and the additional threaded rods being arranged parallel to each other, and an extension of the longitudinal axis of the first additional threaded rod is in fact an axis of symmetry of the loop-shaped pin and lies at the level of the crossing-over of the fixing pins of the support units.

The herein-proposed construction arrangement of the apparatus makes it possible to establish a 'stock' of soft tissues at the distal stump end at a rate faster than the rate of the bone stretching-out.

In addition, a device for osteosynthesis comprising two such apparatus, may have a threaded distraction rod mounted with a possibility of longitudinal travel and of being secured, by means of nuts, in brackets articulately connected to the like ends of the threaded rods.

This makes it possible to simultaneously stretch out two adjacent metacarpal bones and widen the interdigital spaces of the bones being stretched out. In this case the longitudinal axes of the main threaded rods are arranged parallel to the radii of the wrist bones.

SUMMARY OF THE DRAWINGS

In what follows the compression-distraction apparatus of the invention will be illustrated by specific exemplary embodiments thereof with reference to the accompanying drawings, wherein.

PREFERRED EMBODIMENTS OF THE INVENTION

Figure 1:
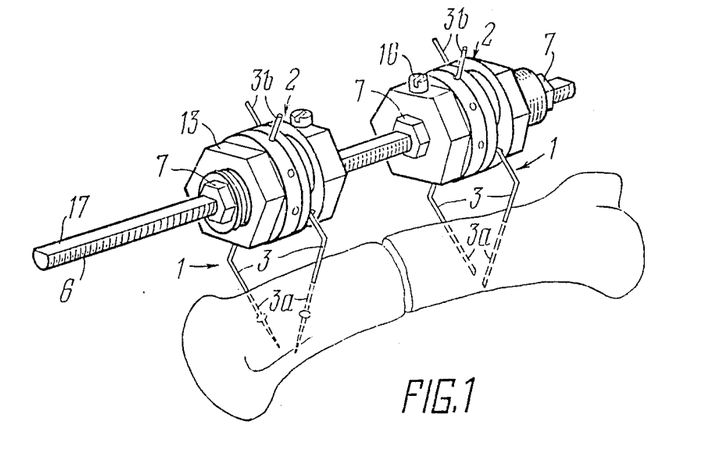
FIG. 1 is a general view of a compression-distraction apparatus for osteosynthesis, according to the invention, when set on the fragments of a short tubular bone.
Figure 2:
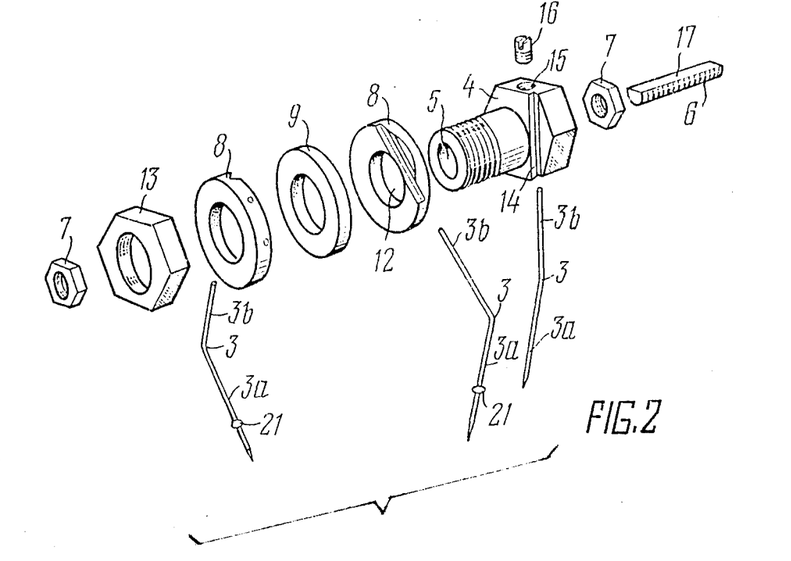
FIG. 2 is an exploded view of the supporting unit of the apparatus, according to the invention.

Now reference is directed to FIG. 1 illustrating the compression-distraction apparatus for osteosynthesis, according to the invention, as a whole and to FIG. 2 showing an exploded view of a support unit of the apparatus.

Figure 3:
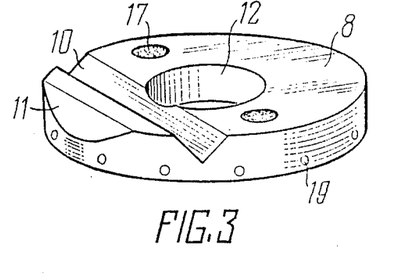
FIG. 3 is the pin holder plate shaped as a washer.

The apparatus, according to the invention, comprises at least two support units 1. Each of the support units 1 incorporates a pin holder 2 carrying fixing pins 3 secured therein. Arms 3a of the pins 3 are crossed in the bone being treated, while arms 3b of the pins 3 are secured in the pin holders 2 in a criss-cross manner. Each of the pin holders 2 is made as a bolt 4 having an axial hole 5 and is longitudinally movable along a main threaded rod 6. Movements are effected by means of nuts 7 located on both sides of the bolt 4 of the pin holder 2. Plates 8 and spacer shims 9 are rotatably mounted on the bolt 4 of the pin holder 2, both the plates 8 (FIG. 3) and the spacer shims 9 (FIG. 4) being shaped as washers. Open slots 10 are made on the end faces of the plate 8. The plate 8 of the pin holder 2 has a flat 11 the plane of which is arranged at an angle to the plate end surface and parallel to the longitudinal axis of the open slot 10. The flat 11 and the open slot 10 are located on the same side of a centre hole 12 in the plate 8. The pins 3 are secured between the end surfaces of the plates 8, the spacer shims 9 and the head of the bolt 4 by a clamping nut 13 (FIGS. 1, 2). An open slot 14 is provided on the end face of the head of the bolt 4 for the pin holder 2 to accommodate the third pin 3.

Apart from that a tapped hole 15 is provided in the head of the bolt 4 square with the axis of the hole 5, wherein a stop screw 16 is fitted. The end of the stop screw 16 is adapted to interact with a flat 17 made on the surface of the main threaded rod 6 lengthwise its axis.

Figure 4:
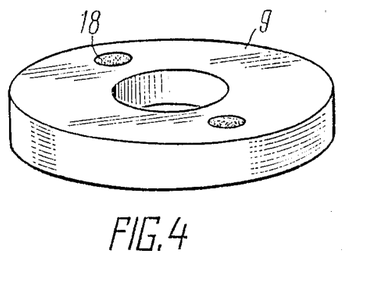
FIG. 4 is the pin holder spacer shim shaped as a washer.

In the embodiments of the apparatus, according to the invention, magnets 17, 18 may be fitted in through holes made in the end surfaces of the plates 8 (FIG. 3) and/or spacer shims 9 (FIG. 4). Recesses 19 may be made in the cylindrical surface of the plates 8.

Figure 5:
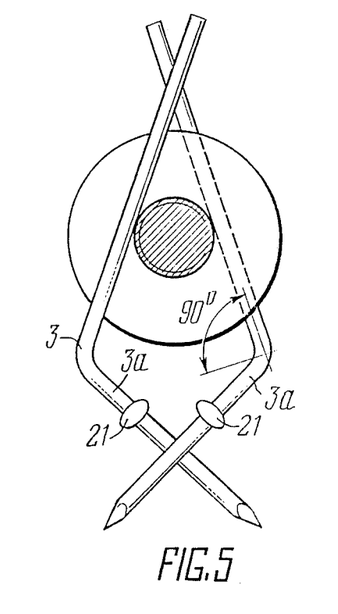
FIG. 5 is an embodiment of the fixing pins attachment in the support unit of the apparatus, according to the invention, showing pin arms curved at an obtuse angle.
Figure 6:
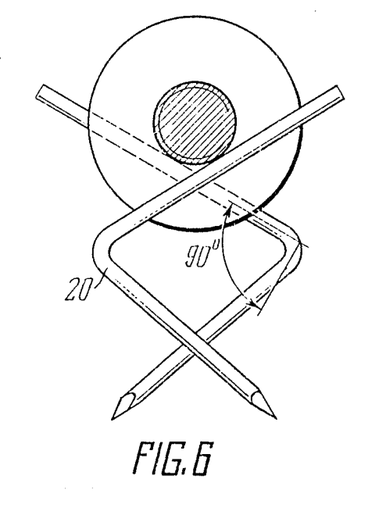
FIG. 6 is an alternative embodiment of the fixing pins attachment in the support unit of the apparatus, according to the invention, showing pin arms curved at an acute angle.

FIG. 5 illustrates an embodiment of the invention, wherein the pins 3 are curved at an obtuse angle, while (FIG. 6 shows pins 20 bent at an acute angle).

Stops 21 may be provided on the arms 3a of the pins 3 to limit the degree of penetration of the latter into the body being treated.

The compression-distraction apparatus for osteosynthesis, according to the invention, may be built up of a required number of the support units depending on treatment tasks to be performed.

Figure 7:
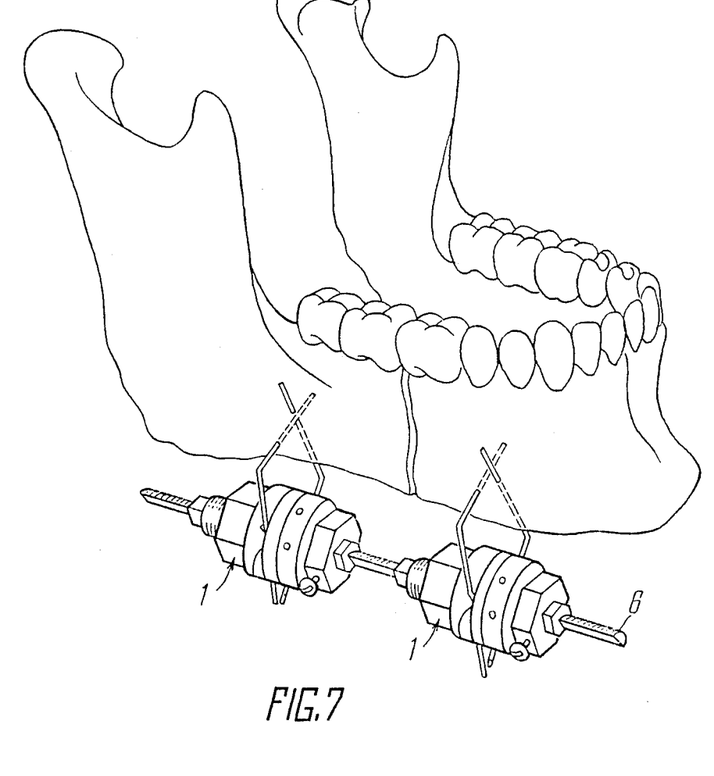
FIG. 7 is a view of the apparatus, according to the invention, when set on an injured mandible.

An apparatus, according to the invention, having two support unit 1 (FIG. 7) is used for fixing short tubular bones, or, e.g., the mandible.

Figure 8:
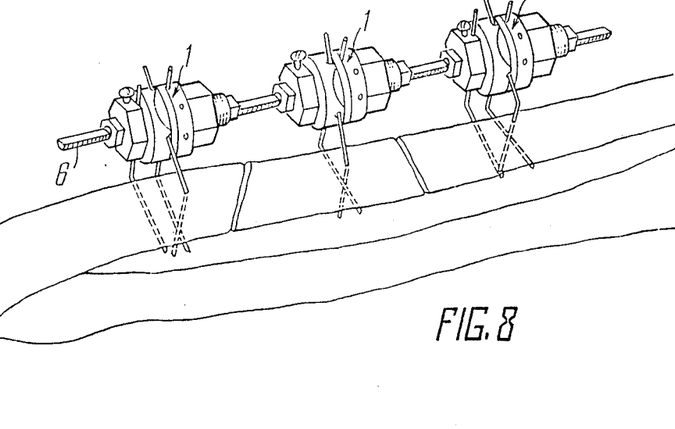
FIG. 8 is a view of the apparatus, according to the invention, having three support units, when set on a long tubular bone with a double fracture.

For fixing long tubular bones use is made of three support units 1 (FIG. 8) fitted on the same main threaded rod 6.

The apparatus, according to the invention, aimed at stretching out a proximally arranged short tubular bone articulately joined to a fragment of the phalangeal stump comprises two support units 1 (FIG. 9) mounted on the main threaded rod 6, which is connected, through a plate 22, to an additional threaded rod 23 carrying an additional support unit 24. The plate 22 has holes 25 through which are passed the main threaded rod 6 and the additional threaded rod 23, both being secured on the plate 22 by screws 26 and 27, respectively.

Figure 10:
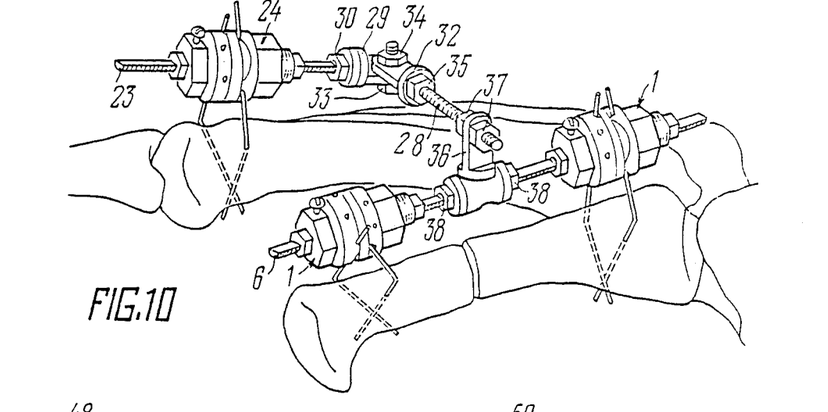
FIG. 10 is an embodiment of the apparatus, according to the invention, having an additional support unit capable of performing angular motion.

To increase the interdigital spaces and simultaneous stretching out of one of the short tubular bones the apparatus, according to the invention, as shown in FIG. 10 comprises two support units 1 mounted on the main threaded rod 6, and an additional support unit 24 mounted on the additional threaded rod 23.

The additional threaded rod 23 is connected to a second additional rod 28. One of the ends of the additional threaded rod 23 is connected to a backet 29 through a nut 30. The bracket 29 is connected to a bracket 32 by means of a bolt 33 and a nut 34 so as to perform angular motion. The bracket 32 is connected to one of the ends of the second additional rod 28 by means of a nut 35, while the other end of the second additional rod 28 is mounted in a bracket 36 with a possibility of longitudinal motion by means of nuts 37. The bracket 36 is located on the main threaded rod 6 between two support units 1 with a possibility of longitudinal travel by means of nuts 38.

Figure 11:
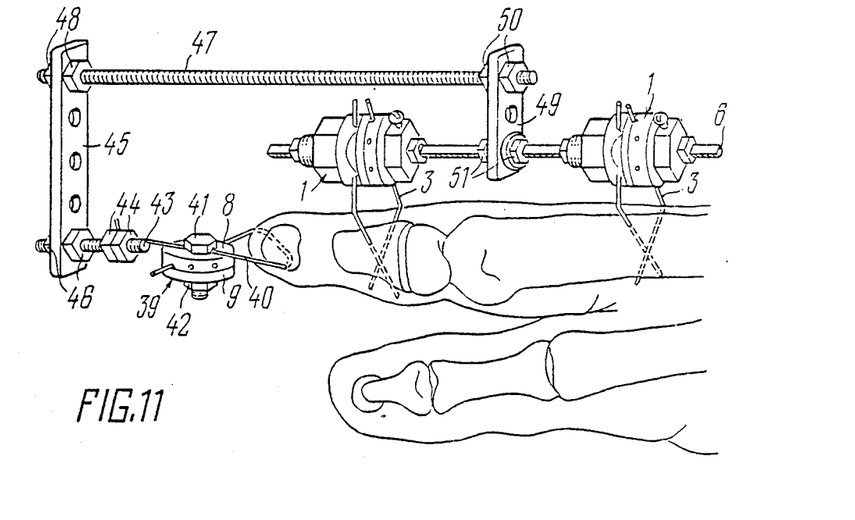
FIG. 11 is an embodiment of the apparatus, according to the invention, having a unit for retraction of soft tissues.

The apparatus, according to the invention, as illustrated in FIG. 11 comprises two support units 1 interconnected by the main threaded rod 6, and a unit 39 for retraction of soft tissue. The unit 39 comprises a pin 40 curved into a loop. The arms of the pin 40 are secured by a nut 42 in a cross-over position between the end surfaces of the plate 8, the spacer shim 9, and the head of a bolt 41. One arm of the pin 40 is fastened to one of the ends of a first additional threaded rod 43 by means of nuts 44, while the other end of the first additional threaded rod 43 is longitudinally movable in a first perforated plate 45 and is locked by nuts 46. One of the ends of a second additional rod 47 is also mounted in the plate 45 with a possibility of longitudinal motion and is held to the plate 45 by nuts 48. The other end of the second additional 47 is fitted in the hole of a second plate 49 and held thereto by nuts 50 so as to execute longitudinal motion. The second plate 49 is fitted, through its hole, on the main threaded rod 6 between the support units 1. The second plate 49 is traversable along the main threaded rod 6 by means of nuts 51. The main threaded rod 6 and two additional threaded rods 43 and 47 are arranged parallel to each other. Besides, the axis of symmetry of the loop-shaped pin 40 is situated at the level of the crossing-over of the pins 3 of the support units 1.

Figure 12:
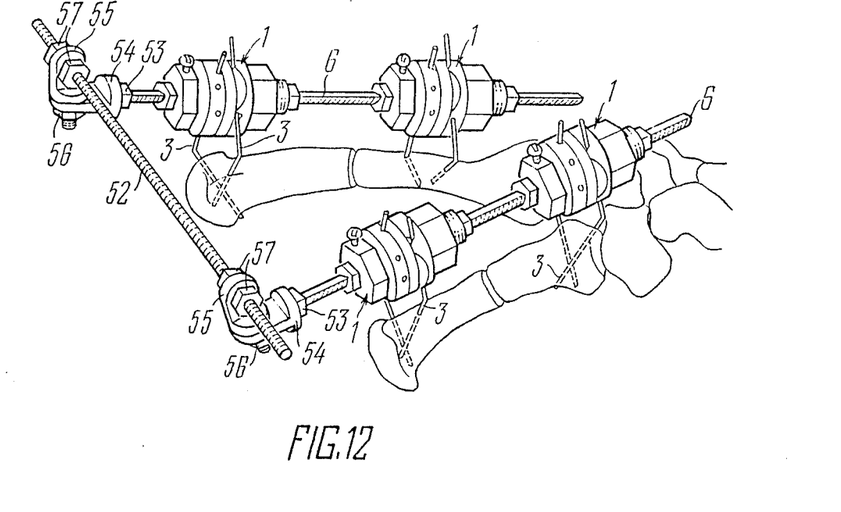
FIG. 12 is an embodiment of a device for osteosynthesis incorporating two apparatus according to the invention.

The device according to the embodiment of the invention illustrated in FIG. 12, comprises two apparatus interconnected through a distraction threaded rod 52. The like ends of the main threaded rods 6 carrying two support units 1 each, are connected to brackets 54 by means of nuts 53. The brackets 54 are connected to brackets 55 through nuts 56. The ends of the distraction threaded rod 52 are fitted in the holes of the brackets 55 and are connected to the latter by nuts 57. Longitudinal traverse of the brackets 55 along the distraction threaded rod 52 is effected by means of the nuts 57.

The compression-distraction apparatus for osteosynthesis of the present invention is applied as follows.

At least two pairs of the fixing pins 3 are introduced into the bone being treated at an angle to each other, the pairs of the pins 3 being arranged distally and proximally. The pins are so introduced at an angle to each other that the point of intersection of each pair of the arms 3a of the distal and proximal pins 3 be located in the bulk of the bone at a depth of the opposite cortical layer.

Apart from that the preoperative procedure includes preparation of a required number of the pin holders 2 of the support unit 1. To do so sets of the plates 8 having the open slots 10 and of the spacer shims 9, as well as the clamping nuts 13 are fitted on the bolts 4 having the axial holes 5.

The arms 3b of the pairs of the proximal pins 3 are to be bent and are arranged in a criss-cross manner successively in the open slots 10 of the plates 8 of the pin holder 2 and are locked in place by the clamping nut 13. One of the pin holders 2 is mounted on the main threaded rod 6 oriented with the aid of the stop screw 16 and locked by the nuts 7. Then the second pin holder 2 is set and the stop screw 16 is drawn tight. The arms of the pairs of the distal pins 3 are bent and fitted in succession in the open slots 10 of the plates 8 of the second pin holder 2 interposed between the nuts 7. The arms 3b of the distal pins 3 are locked by the clamping nut 13. The axis of the main threaded rod 6 is arranged substantially parallel to the longitudinal bone axis.

Whenever necessity arises of installing some additional fixing pins or when it becomes necessary to set and lock the pins 3 in the support unit 1 with the least possible number of the plates 8 and the spacer shims 9, use is made of the open slot 14 provided on the end face of the head of the bolt 4.

To simplify setting and visual control over the direction of the open slot on the end surfaces of the plates 8 of the pin holder 2, use is made of the flat 11 for setting the arms 3b of the pins 3, the plane of the flat 11 being parallel to the axis of the slot 10. To this end, the plate 8 is rotated round the bolt 4 with the aid of some pointed thing, such as a needle or pin, by inserting it into the respective recess 19. Besides, the magnets 17 and 18 are used for short-time keeping of the arm 3b of the pin 3 fitted in the open slot 10, which magnets attract the plates 8 and spacer shims 9 to one another, thus closing the open slot 10 and holding the pin 3 in position.

Once the apparatus has been installed on the bone completely, the stop screws 16 are loosened, the nuts 7 are backed off and the main threaded rod 6 is taken out, whereupon the operation of ostoeotomy is carried out through skin incisions, and the apparatus is reinstalled.

Distraction is effected by moving the pairs of the nuts 7 over the main threaded rod 6. The pairs of the nuts 7 of the distal and proximal pin holders 2 move in the mutually opposite directions.

Rotation of the support unit 1 in the course of its graduated movement along the longitudinal axis of the main threaded rod 6 prevents the stop screw 16 from interacting with the flat 17 of the main threaded rod 6.

Figure 9:
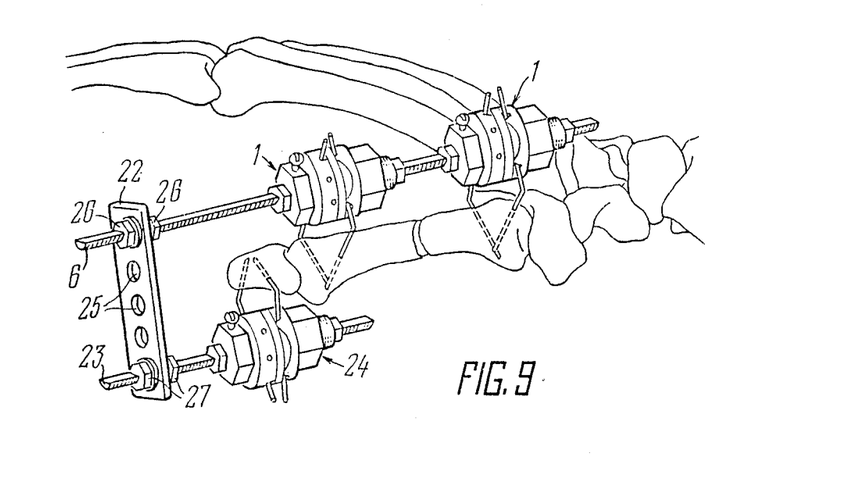
FIG. 9 is an embodiment of the apparatus, according to the invention, having an additional support unit capable of performing translational motion.

Whenever it becomes necessary to provide fixation of a fragment of the phalangeal stump and stretching-out of a proximally arranged short tubular bone joined with the fragment of the phalangeal stump use is made of the additional support unit 24 mounted on the additional threaded rod 23 illustrated in FIG. 9. The additional threaded rod 23 is connected to the main threaded rod 6 by means of the plate 22 and nuts 23, 26. The main threaded rod 6, the additional threaded rod 23, and the axis of the bone being stretched out should be in parallel alignment with one another.

Distraction of the fragment of the phalangeal stump is effected by means of the nuts 23 at a rate advancing the distraction rate of the osteotomized stump fragment carried out by the nuts 26.

In cases where necessity arises for increasing the interdigital spaces and simultaneously stretching out one of the short tubular tubes use is made of the additional support unit 24, wherein the pins 3 are fitted and fixed, in position on the additional threaded rod 23 which is connected, through the nut 30, to the bracket 29. The latter is connected to the bracket 32 through the bolt 33 and the nut 34, as well as to the additional threaded rod 28 by means of the nut 35. The second additional threaded rod 28 is connected to the main threaded rod 6 by means of the bracket 36.

Angular motion is effected by moving the nuts 37 along the second additional threaded rod 28.

One of the possible versions of a general arrangement of the apparatus is the one incorporating the unit for retraction of soft tissues as illustrated in FIG. 11. Soft tissues are retracted by the unit, wherein the pin 40 bent into a loop is passed through the bone fragment (omitted in the Drawing) and clamped with the aid of the plate 8, the spacer shim 9 and the bolt 41 with the nut 42. The arm of the pin is connected to the first additional rod 43 which in turn is connected to the first plate by means of the nuts 46. Then the first plate 45 is connected to the second additional threaded rod 47 by means of the nuts 48, while the second additional threaded rod 47 is connected to the main threaded rod 6 between the support units 1 by means of the second plate 43 and the nuts 50, 51.

All the threaded rods 6, 43, 47 should be parallel to one another and to the axis of the bone being stretched out.

Distraction is carried out by the nuts 46 along the rod 43 at a rate advancing the rate of distraction effected along the main rod 6. The unit for retraction of soft tissues can be traversed by means of the nuts 48, 50 over the second additional rod 47.

Whenever it becomes necessary to simultaneously stretch out two adjacent metacarpal bones and increase the interdigital spaces of the bones being stretched out use is made of the device composed of two apparatus as shown in FIG. 12.

Two apparatus, according to the invention, are placed on adjacent metacarpal bones and the like ends of the main threaded rods 6 are connected, by means of the nuts 53, to the brackets 54 which are connected to the brackets 55 through the nut 56, whereupon the distraction threaded rod 52 is fitted in the holes of the brackets 55.

Distraction is carried out by the nuts 7 of the support units 1 along the main threaded rods 6 simultaneously with distraction effected along the distraction rod 52 of the main threaded rods 6 by the nuts 57, which results in angular motion of the main threaded rods 6, whereby the interdigital spaces are increased.

INDUSTRIAL APPLICABILITY

The herein-proposed compression-distraction apparatus for osteosynthesis can be applied for treatment of fractured finger phalanges or metacarpal bones. Placing the apparatus independently on each of the bone fragments on the palmar surface of the hand makes it possible to avoid contructures of the adjacent joints in the course of treatment, as well as to carry out early and comprehensive bone rehabilitation. Besides, the apparatus may be efficient for arthrodesis application to interphalangeal and metacarpophalangeal joints. When treating the defects of the metacarpal bones the apparatus can be placed not only on the 1st and 5th metacarpal bones but also on the 2nd, 3d and 4th metacarpal bones. The compression-distraction apparatus for osteosynthesis is also applicable for stretching out short tubular bones. The construction of the apparatus makes it practicable for stretching out the digital stumps in cases of developmental anomalies of the wrist bones. In addition, arrangement of a required number of the support units makes it possible to fix the fragment of a phalangeal stump when stretching out the proximally arranged short tubular bone articulately joined with said fragment, as well as to stretch out short tubular bones and simultaneously increase the interdigital spaces. The apparatus is also practicable for treatment of injuries and shortenings of the mandibular bone and long tubular bones. Application of the proposed apparatus places no limitation upon a possibility of patients' self-servicing.

What is claimed is

1. A compression-distraction apparatus for osteosynthesis, comprising at least two support units (1), each incorporating at least two fixing pins (3), one of whose arms (3a) crossing over in the bone, while other arms (3b) are secured in pin holders (2) made as a bolt (4) carrying a set of plates (8) having open slots (10) to accept the fixing pins (3), and a stack of spacer shims (9), the pin holders being fitted on a main threaded rod (6) traversably lengthwise the axis thereof and fixable with the aid of nuts (7), characterized in that the bolt (4) of the pin holder (2) has an axial hole (5) through which the main threaded rod (6) is free to pass, the plates (8) and spacer shims (9) are shaped as washers mounted on the bolt (4) rotatably about its axis and fixable by a clamping nut (13), the open slots (10) to receive the fixing pins (3) are provided on end surfaces of the plates (8) and pass along the chord of their circumference on a far side of the hole (12) in the washer, while the nuts (7) fitted on the main threaded rod (6) are situated on both sides of the bolt ends, and the fixing pins (3) are curved and locked in the pin holder (2) in a criss-cross fashion.

2. An apparatus as claimed in claim 1, characterized in that the pin holder (2) of the support unit (1) is provided with a stop screw (16) fitted in a tapped hole (15) made in a head of the pin holder bolt (4) square with the axis of the bolt hole (5), a flat (17) being provided on the main threaded rod (6) lengthwise thereof, adapted to interact with an end face of the stop screw (16).

3. An apparatus as claimed in claim 1, characterized in that a slot (14) is provided on an end face of the head of the pin holder bolt (4) on a side facing the bolt thread, said slot being adapted for accepting the fixing pin (3).

4. An apparatus as claimed in claim 1, characterized in that each of the pin holder plates (8) having an open slot (10) is shaped as a washer having a flat (11) the plane of which is arranged at an angle to the end surface of the plate (8) and parallel to the longitudinal axis of the slot (10), both the flat (11) and the slot (10) being located on the same side of the hole (12) of the plate (8).

5. An apparatus as claimed in claim 1, characterized in that through holes are provided in the end surfaces of the of the pin holder (2) plates (8) to accommodate magnets (17).

6. An apparatus as claimed in claim 1, characterized in that through holes are provided in end surfaces of the spacer shims (9) of the pin holder (2) to accommodate magnets (18).

7. An apparatus as claimed in claim 1, characterized in that recesses (19) are made on a cylindrical surface of the pin holder plates (8).

8. An apparatus as claimed in claim 1, characterized in that the arms (3a, 3b) of the fixing pins (3) of the support unit (1) are bent at an obtuse angle.

9. An apparatus as claimed in claim 1, characterized in that the arms of the fixing pins (20) of the support unit (1) are curved at an acute angle.

10. An apparatus as claimed in claim 1, characterized in that stops (21) are provided on the arms (3a) of the pins (3) introduced into the bone, aimed at restricting the depth of penetration of the pin (3) into the bone.

11. An apparatus as claimed in claim 1, comprising two support units (1), characterized in that it has an additional support unit (24) mounted on an additional threaded rod (23) movably with respect to the main threaded rod.

12. An apparatus as claimed in claim 11, characterized in that the additional support unit (24) is free to perform relative motion on the additional threaded rod (23) whose longitudinal axis is substantially parallel to that of the main threaded rod (6), said additional threaded rod being relatively movable lenghtwise its own axis.

13. An apparatus as claimed in claim 12, characterized in that it comprises a plate (22) provided with holes (25) which accept the main and additional threaded rods (6,23) connected to the plate (22) through nuts (26,27) located on both sides of the plate (22).

14. An apparatus as claimed in claim 11, characterized in that the additional support unit (24) is mounted on the additional threaded rod (23) connected to the main threaded rod (6) with a possibility of angular motion.

15. An apparatus as claimed in claim 14, characterized in that the additional threaded rod (23) is articulately connected to one end of a second additional rod (28) whose other end is longitudinally movable and is fixable, by means of nuts (37), in a bracket (36) provided on the main threaded rod (6) between two support units (1).

16. An apparatus as claimed in claim 1, comprising two support units (1), characterized in that it has a unit (39) for retraction of soft tissues, comprising a pin (40) curved into a loop whose arms are secured in the pin holder and are free to pass therethrough in a criss-cross fashion so that at least one of the arms of the loop-shaped pin is held to one end of a first additional threaded rod (43), the other end of which is longitudinally movable in a first perforated plate (45), wherein one end of a second additional rod (47) is mounted with a possibility of longitudinal motion, while the other end of said rod is longitudinally traversable in a second perforated plate (49) fitted on the main threaded rod (6) with a possibility of relative motion lengthwise its longitudinal axis, both the main threaded rod (6) and the additional threaded rods (43,47) being arranged parallel to each other, and an extension of the longitudinal axis of the first additional threaded rod (43) is in fact an axis of symmetry of the loop-shaped pin (40) and lies at the level of the cross-over of the fixing pins (3) of the support units (1).

17. A device for osteosynthesis, comprising two apparatus as claimed in any one of claims 1 to 10, placed on adjacent bones, characterized in that it has a threaded distraction rod (52) mounted with a possibility of longitudinal travel and of being secured, by means of nuts (57) in brackets (53) articulately connected to the like ends of the main threaded rods (6).

* * * * *